United States Patent [19]

Beattie et al.

[11] 3,974,151

[45] Aug. 10, 1976

[54] CEPHALOSPORIN COMPOUNDS

[75] Inventors: Thomas R. Beattie, North Plainfield; Burton G. Christensen, Scotch Plains, both of N.J.

[73] Assignee: Merck & Co., Inc., Rahway, N.J.

[22] Filed: June 5, 1973

[21] Appl. No.: 367,256

[52] U.S. Cl. .............................. 260/243 C; 424/246
[51] Int. Cl.² ...................................... C07D 501/20
[58] Field of Search ............................... 260/243 C

[56] References Cited
UNITED STATES PATENTS

| | | | |
|---|---|---|---|
| 3,769,277 | 10/1973 | Long et al. ..................... | 260/243 C |
| 3,780,033 | 12/1973 | Hazen ............................. | 260/243 C |
| 3,780,034 | 12/1973 | Christensen et al. ........... | 260/243 C |
| 3,853,860 | 12/1974 | Weir ............................... | 260/243 C |

*Primary Examiner*—Nicholas S. Rizzo
*Attorney, Agent, or Firm*—Rudolph J. Anderson, Jr.; Julian S. Levitt; James A. Arno

[57] ABSTRACT

Novel 7-methoxy 3-phosphoranylidene cephem compounds which find utility as intermediates in the preparation of antibiotically active 7-methoxy-3-vinyl cephalosporins.

4 Claims, No Drawings

CEPHALOSPORIN COMPOUNDS

This invention relates to novel cephalosporin substances and processes for their preparation. More particularly, it is concerned with novel 7-methoxy 3-phosphoranylidene cephem compounds which find utility as intermediates in the preparation of antibiotically active 7-methoxy-3-vinyl cephalosporins.

In the past several decades, various antibiotic substances have proven to be invaluable in treatment and control of various infections. However, new antibiotics are constantly being sought in order to supplement and expand the physicians armamentarium, particularly for the treatment of infections involving pathogens which have become resistant to the chemotherapeutic agents now in use.

The novel 7-methoxy-3-phosphoranylidenemethyl cephalosporins of the invention may be represented by the structural formula:

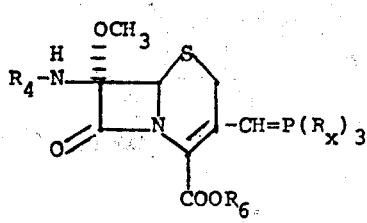

wherein
$R_4$ represents an acyl group, that is conventionally employed in the penicillin and cephalosporin art;
$R_6$ is hydrogen or a carboxyl blocking group;
and $R_x$ is alkyl (preferably lower alkyl of 1–6 carbon atoms; e.g. methyl, ethyl, propyl, n-butyl, t-butyl, pentyl, hexyl); cycloalkyl of 3–8 carbon atoms (e.g. cyclohexyl, cyclopentyl, cyclobutyl etc.); aryl and araliphatic (e.g. phenyl, styryl, benzyl, phenethyl, trityl, cinnamyl, mesityl, tolyl, cumenyl, xylyl.

It should be noted that the above terms are intended to encompass substituted derivatives of said alryl, cycloalryl, aryl and araliphatic moieties wherein the substitutents are selected from halo, nitro, amino, hydroxy, methoxy, etc.

The novel 3-phosphoranylidenemethyl compounds of the invention may be prepared as follows:

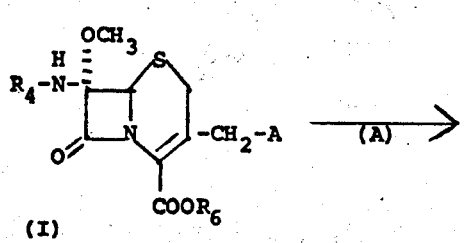

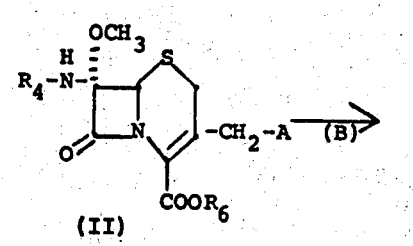

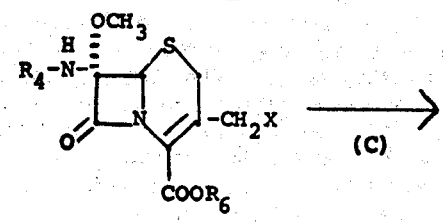

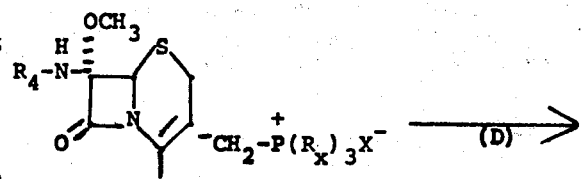

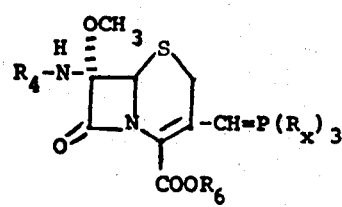

wherein
$R_4$ represents an acyl group conventionally employed in the penicillin and cephalosporin art;
$R_6$ is hydrogen or a carboxyl blocking group;
$R_x$ is alkyl (preferably lower alkyl of 1–6 carbon atoms; e.g., methyl, ethyl, propyl, n-butyl, t-butyl, pentyl, hexyl); aryl and araliphatic (e.g., phenyl, styryl, benzyl, phenethyl, trityl, cinnamyl, mesityl, tolyl, cumenyl, xylyl including substituted derivatives of said alkyl, cycloalkyl, aryl and araliphatic hydrocarbons wherein the substituents are selected from halo, nitro, amino, hydroxy, etc.;

"A" represents iodo, bromo or chloro or a moiety which may conveniently be converted to such group and includes hydrogen, hydroxy, a loweralkoxy or loweralkylthio group, fluoro, an acyloxy or acylthio group. When A represents a loweralkoxy or loweralkylthio group it may be a group such as methoxy, methylthio, tertiary butyloxy, tertiary butylthio, and the like. When A represents an acyloxy or acylthio group it may be a group such as acetoxy, benzoyloxy, cinnamoyloxy, p-sulfocinnamoyloxy, isobutyryloxy, pivaloyloxy, adamantoyloxy, carbamoyloxy, n-methylcarbamoyloxy, N-p-sulfophenylcarbamoyloxy, N-p-carboxymethylphenylcarbamoyloxy, N-chloroethylcarbamoyloxy, N,N-diethyldithiocarbamoyloxy, N,N-dimethylpiperidinodithiocarbamoyloxy, mesyloxy, sulfamoyloxy and 1R:2S-1,2-epoxypropylphosphonyloxy.

X is bromo, chloro is iodo.

The process comprises the following:

A. The $\Delta^3$ 7-methoxy-3CH$_2$A starting material I is converted to the corresponding $\Delta^2$ compound (II) by treatment with an isomerizing agent, preferably a base, for example, an organic base such as an aliphatic or heterocyclic amine such as pyridine, triethylamine and the like or an inorganic base derived from an alkali metal or an alkaline earth metal, for example, an alkali metal or alkaline earth metal carbonate or hydroxide such as sodium carbonate, potassium carbonate, sodium hydroxide, calcium hydroxide and the like. Alumina and silica gel also effect isomerization; however, the organic bases are the preferred isomerizing agents. In general, any inert solvent in which the reactants are soluble may be employed, for example, when an alkali metal or alkaline earth metal base is employed, the solvent is water with a miscible organic solvent such as dioxane, tetrahydrofuran and the like. When an organic base is employed, it may be convenient to use an excess of the organic base as the solvent. The temperature at which the reaction is conducted is not a particularly critical aspect of this invention and, in general, the reaction is conducted at room temperature for a period of time of from about five min. to three days or until isomerization no longer occurs. Isomerization may also be carried out by adsorbing the $\Delta^3$ compound on a chromatography column packed with adsorbent such as Florisil and subsequently desorbing by elution with a solvent such as ethyl acetate.

B. The $\Delta^2$ compound (II) is treated with an agent capable of converting the 3-CH$_2$A group of the cephalosporin molecule to the 3-CH$_2$ X group (III) wherein X is chloro, bromo, or iodo. The reaction may proceed utilizing HCl, HBr or HI at low temperatures ranging from $-30°$ to 25°. A non-protic solvent such as CH$_2$Cl$_2$ or CHCl$_3$ may be used. It will be appreciated of course that where A is chloro, bromo or iodo, step (B) is not necessary and the $\Delta^2$ 3-halomethyl cephalosporin (II) may be treated directly as follows.

C. The 7-methoxy-3-halomethyl cephalosporin (III) is treated with a triorgano phosphine agent to produce the corresponding 3-methyltriorganophosphonium halide (IV). Typical of the solvents that may be employed include ethyl acetate, CH$_2$Cl$_2$, acetone and the reaction may be conducted at temperatures ranging from $-30°$ to 50°.

D. Conversion to the phosphoranylidenemethyl Wittig reagent (V) is effected under basic conditions wherein the pH may vary from about 7.9 to 8.2. Typical of the bases that may be employed include NaOH, K$_2$CO$_3$, Ba(OH)$_2$, LiOMe. Alternatively, the Wittig reagent may be prepared from the phosphonium salt by a process such as dissolving the salt in a solvent such as CH$_2$Cl$_2$ and treating with slightly more than one equivalent of a strong base such as thallous ethoxide at low temperature ($-78°$ to $-30°$).

A further method for preparing the novel 7-methoxy-3-phosphoranylidenemethyl cephalosporins is as follows:

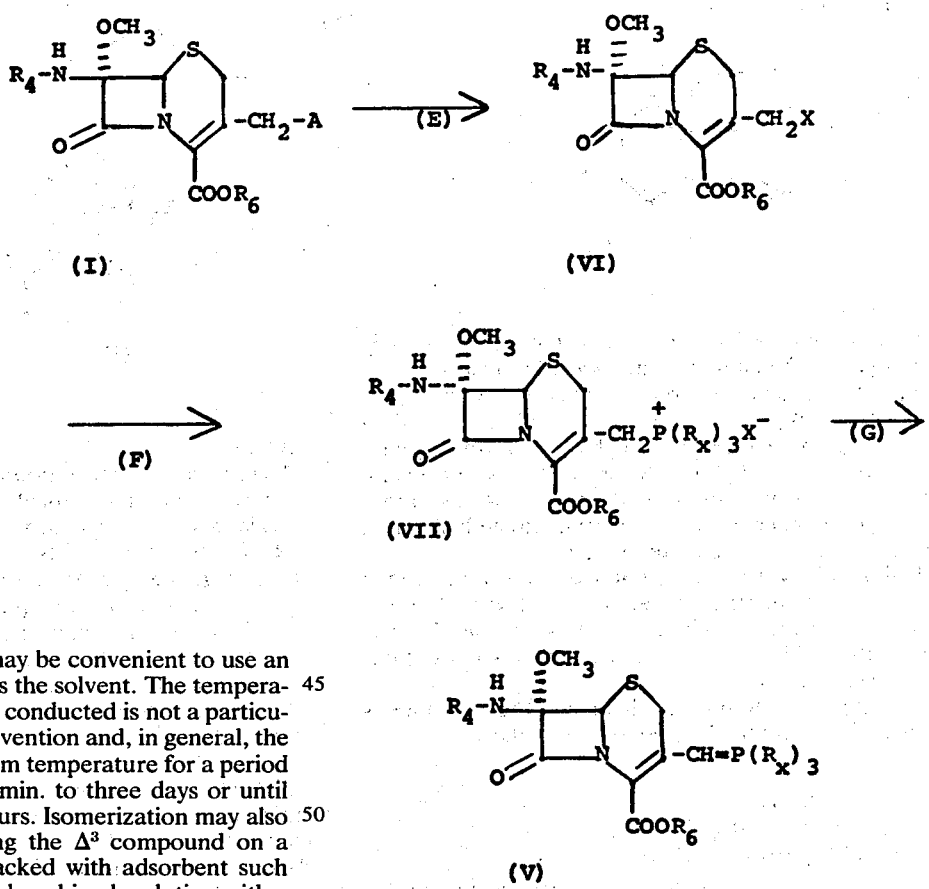

wherein R$_4$, R$_6$, X, R$_x$ and A are as defined above.

The above process comprises the following:

E. The 7-methoxy-3-CH$_2$A starting material (I) is treated with an agent capable of converting the 3-CH$_2$A group of the cephalosporin molecule to the 3-CH$_2$X group (VI) wherein X is chloro, bromo or fluoro. The reaction may proceed utilizing thionyl, chloride, fluoride or bromide, HCl, HBr or HI at low temperatures ranging from $-50°C$ to 25°C. A non-protic solvent such as CH$_2$Cl$_2$ or CHCl$_3$ may be used. It will be appreciated of course that where A is chloro, bromo or fluoro, step (E) is not necessary and the 3-halomethyl cephalosporin may be treated directly as follows.

F. The 7-methoxy-3-halomethyl cephalosporin (VI) is treated with a triorgano phosphine agent to produce the corresponding 3-methyltriorganophosphonium halide (VII). Typical of the solvents that may be employed include ethyl acetate, carbon tetrachloride, dioxane acetone and methylene chloride and the reaction may be conducted at temperatures ranging from −20°C to 50°C.

G. Conversion to the phosphoranylidenemethyl Wittig reagent (V) is effected under basic conditions wherein the pH may vary from about 7.9 to 8.2. Typical of the bases that may be employed include NaOH, $K_2CO_3$, $Ba(OH)_2$, LiOMe. Alternatively, the Wittig reagent may be prepared from the phosphonium salt by a process such as dissolving the salt in a solvent such as $CH_2Cl_2$ and treating with slightly more than one equivalent of a strong base such as thallous ethoxide at low temperature (−78° to −30°).

Illustrative of the triorganophosphine agents that may be employed in the practice of the invention are trialkyl-, tricycloalkyl-, triaryl-, and triaraliphatic phosphines. It will be appreciated that the terms alkyl, aryl, cycloalkyl and araliphatic are intended to encompass substituted derivatives of said terms.

Illustrative of the representative members of the class of triorgano phosphine agents that may be employed in the practice of the invention includes the following: triphenylphosphine, tri(p-nitrophenyl)phosphine, tri-(p-chlorophenyl)phosphine, tri(o-nitrophenyl)phosphine, tri(m-chlorophenyl)phosphine, tri(cyclohexyl)phosphine, tri(t-butyl)phosphine, tri(n-butyl)phosphine, trimethylphosphine, triethylphosphine, and tri(m-nitrophenyl)phosphine.

The acyl radical represented by $R_4$ can be substituted or unsubstituted aliphatic, aromatic or heterocyclic, araliphatic or heterocyclyaliphatic carboxylic acid radical or a carbothioic acid radical such as the acyl radicals of the known cephalosporins and penicillins. These acyl radicals can be represented by the general formula

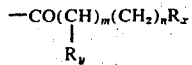

where $R_y$ is a radical of the group defined below, $m$ and $n$ represent 0–4 and $R_x$ represents R″ or ZR″, which are defined below.

The following compilation of acyl groups illustrated below are merely representative and not intended to be exhaustive.

One group of acyl radicals can be represented by the acyl group general formula:

wherein R″ represents a substituted or unsubstituted straight or branched chain alkyl, alkenyl or alkynyl group; aryl, aralkyl; cycloalkyl; or a heteroary or heteroaralkyl group. These groups can be unsubstituted or can be substituted by radicals such as alkyl, akoxy, halo, cyano, carboxy, sulfoamino, carbamoyl, sulfonyl, azido, amino, substituted amino, haloalkyl, carboxyalkyl, carbamoylalkyl, N-substituted carbamoylalkyl, guanidino, N-substituted guanidino, quanidinoalkyl, and the like. Representative examples of such acyl groups that might be mentioned are those wherein R″ is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β, β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isozazolyl, 3-butyl-5-methyl-4-isoxazolyl, 5-methyl-3-phenyl-4-isoxazolyl, 3-(2-chlorophenyl)-5-methyl-4-isoxazolyl, 3-(2-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl) methyl, 2- or 3-(5-methylthienyl)methyl, 2- or 3-(5-methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and tetrazolylmethyl.

The acyl group can also be a radical of the formula

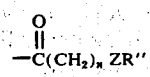

wherein $n$ is 0–4, Z represents oxygen or sulfur, and R″ is defined as above. Representative members of the substituent

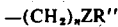

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-(carboxymethyl)phenylthiomethyl, 2-pyrimidinylthiomethyl, phenylthiomethyl, 1-(5,6,7,8-tetrahydronaphthyl)oxometyl, 6,8-bis (methylthio)octanoyl, Alternatively, the acyl group can be a radical of the formula

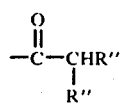

wherein R'' is defined as above and R''' is a radical such as amino, hydroxy, azido, carbamoyl, guanidino, acyloxy, halo, sulfamino, tetrazolyl, sulfo, carboxy, carbalkoxy, and the like. Representative members of the substituent

that might be mentioned are α-aminobenzyl, α-amino-2-thenyl, α-methylaminobenzyl, α-amino-γ-methylmercaptopropyl, α-amino-3 or 4-chlorobenzyl, α-amino-3 or 4-hydroxybenzyl, α-amino-2, 4-dichlorobenzyl, α-amino-3, 4-dichlorobenzyl, D(-)-α-hydroxybenzyl, α-carboxybenayl, α-amino-3-thenyl, α-amino-2-thenyl, D(-)-α-amino-3-chloro-4-hydroxybenzyl, D(-)-α-amino-3-thenyl, 1-aminocyclohexyl, α-(5-tetrazolyl)benzyl, α-sulfaminobenzyl, α-sulfamino-3-thenyl, α-(N-methylsulfamino)-benzyl, D(-)-α-guanidino-2-thenyl, D(-)-α-guanidionbenzyl, α-guanylureidobenzyl, α-hydroxybenzyl, α-azidobenzyl, α-fluorobenzyl, 4-(5-methoxy-1,3-oxadiazole)-aminomethyl, 4-(5-methoxy-1,3-oxadiazole)-hydroxymethyl, 4-(5-methoxy-1,3-oxadiazole)-carboxymethyl, 4-(5-methoxy- 1,3-sulfadiazole)-aminomethyl, 4-(5-methoxy-1,3-sulfadiazole)-hydroxymethyl, 4-(5-methoxy-1,3-sulfadiazole)-carboxymethyl, 2-(5-chlorothienyl)-aminomethyl, 2-(5-chlorothienyl)hydroxymethyl, 2-(5-chlorothienyl)-carboxymethyl, 3-(1,2-thiazole)-aminomethyl, 3-(1,2-thiazole)-hydroxymethyl, 3-(1,2-thiazole)-carboxymethyl, 2-(1,4-thiazolyl)-aminomethyl, 2-(1, 4-thiazolyl)-hydroxymethyl, 2-(1, 4-thiazolyl) aminomethyl, 2-(1,4-thiazolyl)-hydroxymethyl, 2-(1,4-thiazoyly)-carboxymethyl,2-benzothienylamino ethyl, 2-benzothienylhydroxymethyl, 2-benzothienylcarboxymethyl, 2-azidooctyl-3-phenyl13azidomethyl, α-sulfobenzyl, and α-phosphonobenzyl.

Alternatively, the group

can be a sulfonamido group such as phenylsulfonamido, ethylsulfonamido, benzylsulfonamido, 2,5-dimethylsulfonamido, 4-chlorosulfonamido, 4-chlorophenylsulfonamido, 4-methoxysulfonamido, and the like.

The acyl substituents of the general formula

wherein $R_{10}$ and $R_{11}$ are as defined below represent a preferred group of substituents because of their generally useful antibiotic activity. $R_{10}$ represents hydrogen, halo, amino, guanidino, phosphono, hydroxy, tetrazolyl, carboxy, sulfo or sulfamino. $R_{11}$ represents phenyl, substituted phenyl, a monocyclic heterocyclic 5- or 6-membered ring containing one or more oxygen, sulfur or nitrogen atoms in the ring, substituted heterocycles, phenylthio, heterocyclic or substituted heterocyclic thio groups; or cyano. The substituents can be halo, carboxymethyl, guanidino, guanidinomethyl, carboxamidomethyl, aminomethyl, nitro, methoxy or methyl. Examples of these preferred substituents that might be mentioned are phenacetyl, 3-bromophenylacetyl, p-aminomethylphenylacetyl, 4-carboxylmethylphenylacetyl, 4-carboxyamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thineylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiaxolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5 -thiadiazolyl-4-acetyl, phenylthioacetyl, 4-pyridylthioacetyl, cyanoacetyl, tetrazolylacetyl, α-fluorophenylacetyl, D-phenylglycyl, Y-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

Pursuant to a preferred embodiment of this invention, $R_4$ is represented by the formula

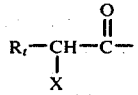

wherein X is hydrogen, halogen, amino, guanidino, phosphono, hydroxy, tetrazolyl, carboxy, sulfo, or sulfamino; $R_t$ is phenyl, substituted phenyl, a monocyclic heterocyclic 5- or 6-membered ring containing one or more oxygen, sulfur or nitrogen atoms in the ring, substituted heterocycles, phenylthio, phenyloxy, heterocyclic or substituted heterocyclic thio groups, lower alkyl (1–6 carbon atoms), or cyano; the substituents on the $R_t$ group being halo, carboxymethyl guanidino, guanidinomethyl, carboxamidomethyl, aminomethyl, nitro, methoxy or methyl. Particularly preferred are acyl groups where X is hydrogen, hydroxy, amino or carboxy and $R_t$ is phenyl, lower alkyl or a 5- or 6-membered heterocyclic ring having one or two sulfur, oxygen or nitrogen hetero atoms. Specific $R_t$ substituents that might be mentioned as preferred include thiazolyl, thienyl, furyl and phenyl.

The carboxyl blocking group ($R_6$) is, preferably, an ester formed with an alcohol or phenol.

Generally, it is preferred to carry out the reaction with a cephalosporin compound wherein the carboxy group is blocked or protected since maximum yields of the desired product are obtained with such derivatives. It is preferable that a protecting group be utilized which can be removed to obtain the free acid without disruption of the β lactam moiety.

The group protecting the 4-carboxyl group may be formed with an alcohol (aliphatic or araliphatic), phenol, silanol, stannanol or acid which may readily be split off at a later stage of the reaction.

Suitable esters thus include compounds containing as the 4-ester group, a group selected from the following list which is representative and not intended to be an exhaustive list of possible ester groups:

i. - COOCR$^a$R$^b$R$^c$ wherein at least one of R$^a$, R$^b$ and R$^c$ is an electron-doner e.g. p-methoxyphenyl, 2,2,6-trimethylphenyl, 9-anthryl, methoxy, acetoxy, tetrahydrofur-2-yl, tetrahydropyran-2-yl or fur-2-yl. The remaining R$^a$, R$^b$ and R$^c$ groups may be hydrogen or organic substituting groups. Suitable ester groups of this type include p-methoxybenzyloxycarbonyl and 2,4,6-trimethylbenzyloxycarbonyl.

ii. - COOCR$^a$R$^b$R$^c$ wherein at least one of R$^a$, R$^b$ and R$^c$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining R$^a$, R$^b$ and R$^c$ groups may be hydrogen or organic subsubstituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl, iii. - COOCR$^a$R$^b$R$^c$ wherein at least two of R$^a$, R$^b$ and R$^c$ are hydrocarbon such as alkyl e.g. methyl or ethyl, or aryl e.g. phenyl and the ramaining R$^a$, R$^b$ and R$^c$ group, if there is one, is hydrogen. Suitable esters of this type include, t-butyloxycarbonyl, t-amyloxycarbonyl, diphenylmethoxycarbonyl and triphenylmethoxycarbonyl.

iv. - COOR$^d$ wherein R$^d$ is adamantyl, 2-benzyloxyphenyl, 4-methylthiophenyl or tetrahydropyran-2-yl.

Silyl esters may conveniently be prepared from a halosilane or a silazane of the formula R$^4{}_3$SiX; R$^4{}_2$SiX$_2$; R$^4{}_3$Si.NR$^4{}_2$; R$^4{}_3$SiR$^4{}_3$; R$^4{}_3$Si.NH.COR$^4$; R$^4{}_3$Si.NH.CO.NH.SiR$^4{}_3$; R$^4$NH.CO.NR$^4$.SiR$^4{}_3$; or R$^4$C(OSiR$^4{}_3$):

NSiR$^4{}_3$ where X is a halogen and the various groups R$^4$, which can be the same or different, represent hydrogen atoms or alkyl, e.g. methyl, ethyl, n-propyl, iso-propyl; aryl, e.g. phenyl; or aralkyl e.g. benzyl groups.

Preferred derivatives of silanols are silyl chlorides such as for example trimethylchlorosilane and dimethyldichlorosilane.

Protecting groups of particular interest include alcohols and phenols, and the like. R$_6$ is preferably an alkyl or aralkyl group containing from 1 to about 20 carbon atoms. Thus, R$_6$ can be a lower alkyl group such as methyl, ethyl or tertiary butyl, a substituted alkyl such as phthalimidomethyl, succinimidomethyl, phenacyl, substituted phenacyl such as p-bromophenacyl, a β-substituted ethyl group such as 2,2,2-trichloroethyl, 2-methylthioethyl or 2-(p-methylphenyl)ethyl, an alkoxyalkyl group such as methoxymethyl, an aryloxyalkyl such as p-methoxyphenoxymethyl, an aralkyloxyalkyl group such as benzyloxymethyl, a substituted benzyl group such as p-nitrobenzyl, p-methoxybenzyl, 3,5-dinitrobenzyl, 2,4,6-trimethylbenzyl or 3,5-dichloro-4-hydroxybenzyl, benzhydryl or a substituted benzhydryl group such as p-methoxybenzhydryl, and the like. Preferred blocking groups are methyl, tertiary butyl, phenacyl, p-bromophenacyl, 2,2,2-trichloroethyl, p-methoxybenzyl, benzhydryl, methoxymethyl and p-methoxyphenoxymethyl.

The term "blocking group" as utilized herein is employed in the same manner and in accordance with the teaching of U.S. Pat. No. 3,697,515; the contents therein with respect to said blocking group being incorporated herein by reference.

In addition to blocking the carboxy group, it is generally preferred to block or protect any amino groups present in the starting materials since maximum yields of the desired products are obtained with such derivatives. For this purpose, the groups are preferably blocked with substitutents that are readily removed. Such groups are well known in the art. For example, the amino group is most conveniently blocked by a group such as trichloroethoxycarbonyl, t-butoxycarbonyl, benzoylmethoxycarbonyl, trimethylsilyl, p-methoxybenzyloxy, o-nitrophenylthio, and the like.

Representative of the 7-methoxy-3-phosphoranylidenemethyl cephalosporins of the invention are the following:

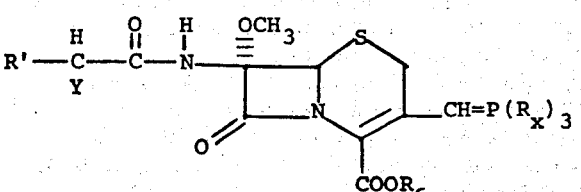

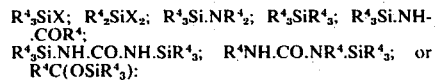

| R$_r$ | R' | Y | R$_6$ |
|---|---|---|---|
| phenyl | 2-thienyl | H | benzhydryl |
| p-nitrophenyl | 2-furyl | H | benzyl |
| p-chlorophenyl | phenyl | H | trichloroethyl |
| o-nitrophenyl | 2-thiazolyl | H | methoxymethyl |
| m-chlorophenyl | phenyl | NH$_2$ | benzhydryl |
| cyclohexyl | phenyl | OH | benzyl |
| n-butyl | 2-thienyl | H | trichloroethyl |
| o-nitrophenyl | 2-furyl | H | methoxymethyl |
| m-nitrophenyl | phenyl | H | p-methoxybenzyl |
| phenyl | 2-thiazolyl | H | methyl |
| cyclohexyl | phenyl | CO$_2$H | t-butyl |
| n-butyl | phenyl | OH | 2,2,2-trichloroethyl |
| n-butyl | 2-thienyl | H | benzhydryl |
| phenyl | 2-furyl | H | benzyl |
| p-nitrophenyl | phenyl | H | trichlorethyl |
| p-chlorophenyl | 2-thiazolyl | H | methoxymethyl |
| o-nitrophenyl | phenyl | NH$_2$ | benzhydryl |
| m-chlorophenyl | phenyl | OH | benzyl |
| cyclohexyl | 2-thienyl | H | trichloroethyl |
| n-butyl | 2-furyl | H | methoxymethyl |
| o-nitrophenyl | phenyl | H | p-methoxybenzyl |
| m-nitrophenyl | 2-thiazolyl | H | methyl |
| phenyl | phenyl | NH$_2$ | t-butyl |
| cyclohexyl | phenyl | OH | 2,2,2-trichloroethyl |
| o-nitrophenyl | 2-thienyl | H | benzhydryl |
| m-nitrophenyl | 2-furyl | H | benzyl |
| phenyl | phenyl | H | trichloroethyl |
| cyclohexyl | 2-thiazolyl | H | methoxymethyl |
| n-butyl | 3-thienyl | CO$_2$H | benzhydryl |
| p-chlorophenyl | phenyl | OH | benzyl |
| phenyl | 2-thienyl | H | trichloroethyl |
| p-nitrophenyl | 2-furyl | h | methoxymethyl |
| p-chlorophenyl | phenyl | H | p-methoxybenzyl |
| o-nitrophenyl | 2-thiazolyl | H | methyl |
| m-chlorophenyl | phenyl | OH | t-butyl |
| cyclohexyl | phenyl | NH$_2$ | 2,2,2-trichloroethyl |

The starting materials in the foregoing processes may be 7-methoxy-3-CH$_2$A cephalosporins wherein A is either Cl, Br or I or a group which may be converted to a Cl, Br or I substituent. The 7-methoxy-3-CH$_2$A cephalosporins that are employed as the starting materials for the preparation of the novel 7-methoxy-3-phosphoranylidene compounds of the invention are well known and processes for their preparation are set forth in Belgium Patent 718,528 issued Dec. 15, 1971.

Illustrative of the procedures that may be employed to produce the 7-methoxy cephalosporin Wittig reagent is the following

EXAMPLE 1

Preparation of benzhydryl 3-carbamoyloxymethyl-7α-methoxy-7β-(-thienylacetamido)3-cephem-4-carboxylate To a stirred slurry of 15 g. (0.0352 mole) of 3-carbamoyloxymethyl-7α-methoxy-7β-(2-thienylacetamido)3-cephem-4-carboxylate in 300 ml. acetonitrile is added 6.83 g. (0.0352 mole) of diphenyldiazomethane in 100 ml. acetonitrile during 4 hr. at 22°C. After completion of addition a small quantity (0.5 g.) of dark solid is removed by filtration and discarded. After stirring for 17 hr. at 22° the pale yellow solution is used in the next step directly.

The benzhydryl 3-carbamoyloxymethyl-7α-methoxy-7β-(2-thienylacetamido)3-cephem-4-carboxylate product has the following NMR spectrum: NMR(CDCl$_3$): 3.43δ broad s, 2-CH$_2$; 3.51δ S, 3H, O—CH$_3$; 3.87δ, S, 2H,

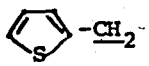

4.6–5.0δ broad multiplet; 5.08δ, S, 1H, C-6H; ≈7.0δ, multiplet

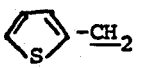

7.33δ, Ph.

EXAMPLE 2

Preparation of benzhydryl 3-carbamoyloxymethyl-7α-methoxy-7β-(2-thienylacetamido)2-cephem-4-carboxylate To the reaction solution obtained in Example 1 is added 1 ml. triethylamine. The solution is stirred at 22°C. for 1 hr., during which time it darkens progressively. The solvent and triethylamine are removed under reduced pressure and the residue, benzhydryl 3-carbamolyoxymethyl-7α-methoxy-7β-(2-thienylacetamido)2-cephem-4-carboxylate, is used directly in the next step. The product weighed 20.5 g.

The product has the following NMR spectrum: NMR(CDCl$_3$): 3.41δ, S, 3H, —OCH$_3$; 3.85δ, S, 2H,

4.58δ, S; 4.81δ, S; 5.10δ, S; 5.33δ, S; 6.38 δ, sl. split broad singlet, 1H,

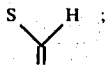

6.97δ, m.,

7.37δ, S, Ph.

EXAMPLE 3

Preparation of benzhydryl 3-chloromethyl-7α-methoxy-7β-(2-thienylacetamido)2-cephem-4-carboxylate The benzhydryl 3-carbamoyloxymethyl-7α-methoxy-7β-(2-thienylacetamido)2-cephem-4-carboxylate from the above reaction is dissolved in 200 ml. of methylene chloride and stirred in an ice bath under a nitrogen atmosphere. Gaseous hydrogen chloride is bubbled into the solution slowly. The progress of the reaction is followed by t.l.c. (EtOAc/PhH:1/3, silica gel G 1 × 4 plates, developed with ceric sulfate in aqueous sulfuric acid spray). Within 15 minutes the solution becomes cloudy and the reaction is over within 3 hours. The reaction mixture is evaporated under reduced pressure and flushed with methylene chloride and re-evaporated twice to remove hydrogen chloride. The benzhydryl 3-chloromethyl-7α-methoxy-7β-(2-thienylacetamido)2-cephem-4-carboxylate obtained is dissolved in 150 ml. methylene chloride, filtered to remove ammonium chloride, evaporated, and used in the next step directly.

Anal. Calcd. for $C_{28}H_{25}ClN_2O_5S_2$: C, 59.09; H, 4.43; N, 4.92. Found: C, 59.82; H, 4.54; N, 4.48.

Mass spectrum shows peaks at 568 (M+), 534, 488, 400, 358, 277, 240, 210, 204 and 167.

EXAMPLE 4

Preparation of benzhydryl 3-iodomethyl-7α-methoxy-7β-(2-thienylacetamido)-2-cephem14-carboxylate The benzhydryl 3-chloromethyl-7α-methoxy-7β-(2-thienylacetamido)2-cephem-4-carboxylate from the previous step and 75 ml. acetone is stirred in an ice bath and 8.0 g. sodium iodide in 50 ml. ice cold acetone is added. After 4 hours of stirring in an ice bath the mixture is evaporated under reduced pressure and 100 ml. of methylene chloride is added. The mixture is filtered and the solid washed well with methylene chloride. The filtrate and washings are evaporated under reduced pressure and the benzhydryl 3-iodomethyl-7α-methoxy- 7β-(2-thienylacetamido)s-2-cephem -4 -carboxylate is obtained and used directly in the next step.

The product has the following NMR spectrum: NMR(CDCl$_3$): 3.43δ, S, 3H, )CH$_3$; 4.10 δ, AB quartet, —CH$_2$I; 5.39δ, multiplet; 6.43δ, br.s., 1H, 7.0δ, m.,

7.37δ, S, Ph.

EXAMPLE 5

Preparation of
[4-diphenylmethoxycarbonyl-7α-methoxy-7β-(2-thienylacetamido)-2-cephem-3-ylmethyl]triphenylphosphonium iodide The crude benzhydryl 3-iodomethyl-7α-methoxy-7β-(2-thienylacetamido)-2-cephem-4-carboxylate from the last reaction is dissolved in 150 ml. of ethyl acetate, cooled and stirred in an ice bath, and 18 g. of triphenylphosphine is added. Within 5 minutes the solution becomes cloudy. After stirring for 1 hour at 0°C. and 4 hours at 22°C. the liquid is decanted and the solid is washed with ethyl acetate. The residue is taken in 30 ml. methylene chloride and 300 ml. ethylacetate is added to precipitate the [4-diphenylmethoxycarbonyl-7α-methoxy-7β-(2-thienylacetamido)-2-cephem-3-ylmethyl]triphenylphosphonium iodide. The product is obtained by filtration and drying, has a m.p. 107°dec. and foams slowly as heating continues.

Anal. Calcd. for $C_{46}H_{40}N_2IO_5S_2P$: C, 59.87; H, 4.37; N, 3.04. Found: C, 59.24; H, 4.02; N, 2.57.

EXAMPLE 6

Preparation of benzhydryl
3-(triphenylphosphoranylidenemethyl)-7α-methoxy-7β-(2-thienylacetamido)-3-cephem-4-carboxylate To a solution of 1.518 g. of [4-diphenylmethoxycarbonyl-7α-methoxy-7β-(2-thienylacetamido)-2-cephem-3-ylmethyl]triphenylphosphonium iodide, 18 ml. acetone and 2.4 ml. water cooled and stirred in an ice bath is added 18 drops 2N sodium hydroxide to bring the pH to 7.9–8.2. The addition of 10 ml. water causes an oil to appear which is extracted into methylene chloride, dried with anhydrous magnesium sulfate and evaporated under reduced pressure to afford 1.18 g. of benzhydryl 3-(triphenylphosphoranylidenemethyl)-7α-methoxy-7β-(2-thienylacetamido)-3-cephem-4-carboxylate.

The product had the following NMR: NMR(CDCl₃): 2.6δ, AB quartet, 2H,

3.50δ, S, 3h, OCH₃; 3.74δ, S, 2H,

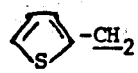

5.08δ, 1H, S, C-6H; 5.42δ, doublet, J=31 cps, 1H, —CH=PPH₃; 6.7–7.8δ, aromatic protons, m.

EXAMPLE 7

Preparation of benzhydryl
7-methoxydesacetylcephalothin

To an ethyl acetate solution (300 ml) of 7-methoxydesacetylcephalothin (4g) is added 2.0 g of diphenyldiazomethane as a solid. After 3 hours, the reaction mixture is concentrated in vacuo to a small volume (15 ml) which is kept at 0°–5° overnight. The precipitate is collected and dried to give benzhydryl 7-methoxydesacetylcephalothin.

EXAMPLE 8

Preparation of benzhydryl 7β-thiopheneacetamido-7-methoxy-3-chloromethylceph-3-ene-4-carboxylate A solution of 7-methoxydesacetylcephalothin (1.77 g., 3.4 mmoles) in tetrahydrofuran (13.5 ml) containing pyridine (0.40 ml. 6.8 mmoles) is chilled to −25°. Thionyl chloride (0.49 ml. 6.8 mmoles) in 5 ml. of tetrahydrofuran is added over a 40-minute period. After an additional hour, the mixture is poured into n-HCl which has been saturated with salt. The aqueous phase is extracted (2 × 30 ml) with ethyl acetate. The combined organic layers are worked with 5% sodium bicarbonate and water, dried and concentrated in vacuo to give benzhydryl 7β-thiopheneacetamido-7-methoxy-3-chloromethylceph- 3-ene-4-carboxylate,

EXAMPLE 9

Preparation of benzhydryl
7β-thiopheneacetamido-7-methoxy-3-iodomethyl-ceph-3-ene-4-carboxylate a solution of benzhydryl 7β-thiopheneacetamido-7-methoxy-3-chloromethylceph-3-ene-4-carboxylate (0.25 g) in acetone (5 ml) is added to a solution of sodium iodide (0.25 g) in acetone (2ml). The mixture is allowed to stand in the dark for 2 hours, poured into brine and extracted into ethyl acetate. The organic layer is washed with a 5% sodium thiosulfate solution and water, dried and concentrated in vacuo to give benzhydryl  7β-thiopheneacetamido-7-methoxy-3-iodomethylceph-3-ene-4-carboxylate.

EXAMPLE 10

Preparation of
[4-diphenylmethoxycarbonyl-7β-thiopheneacetamido-ceph-3-em-3-ylmethyl]triphenylphosphonium iodide To a solution of benzhydryl 7β-thiopheneacetamido-7-methoxy-3-iodomethylceph-3-ene-4-carboxylate (0.15 g) in ethyl acetate (2.5 ml) is added a solution of triphenylphosphine (0.125 g) in ethyl acetate (2ml) over a 45-minute period in the dark. The mixture is allowed to stand another hour in an ice-bath and the product [4-diphenylmethoxycarbonyl-7β-thiopheneacetamido-cephl3-em-3-ylmethyl]triphenylphosphonium iodide collected by filtration.

EXAMPLE 11

Preparation of benzhydryl
7β-thiopheneacetamido-7-methoxy-3-(triphenylphosphoroanylidenemethyl)-ceph-3-em-4-carboxylate To a solution of [4-diphenylmethoxycarbonyl-7β-thiopheneacetamido-ceph-3-em-3-ylmethyl]triphenylphosphonium iodide (0.1 g) in acetone:water (12 ml:2 ml) is added in an ice-bath and the pH adjusted to pH 11 with 2N sodium hydroxide. The reaction mixture is diluted with an equal volume of solvent and filtered. The precipitate is washed with acetone and ether and dried to give benzhydryl 7β-thiophenacetamido-7-methoxy-3-(triphenylphosphoroanylidenemethyl)-ceph-3-em-4-carboxylate.

As disclosed in copending application Ser. No. 367,291, filed of even date with the present application in the names of T. R. Beattie, D. B. R. Johnston, and J. Hannah, entitled Novel Cephalosporin Compounds and Processes for Their Preparation, Disclosure No. D 72/108, Case No. 15405, and incorporated herein by reference, the novel 3-phosphoranylidenemethyl cephalosporins of the present invention are useful as intermediates in the preparation of 3-vinyl cephalosporin compounds which are active against a range of gram-negative and gram-positive microoragnisms and are of value in human and veterinary medicine.

The procedure by which the antibiotically active 3-vinyl cephalosporins may be prepared via the novel phosphoranylidenemethyl compounds involves the reaction of a novel phosphoranylidene compound of the formula:

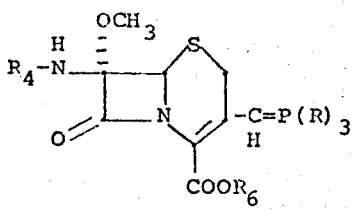

with a carbonyl compound of the formula $R_2$—CO—$R_3$ to produce 3-vinyl cephalosporins of the formula:

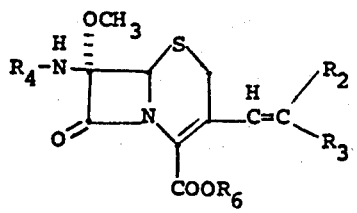

wherein $R_6$ is H or a carboxyl blocking group;

$R_4$ represents an acyl group;

$R_2$ and $R_3$ may be the same or different and are each selected from the following: hydrogen, aryl, heterocyclic aromatic, alkyl, cycloaliphatic, carboxyl, cyano, -$SO_2NR_4R_5$, -P(O) (O$R_4$)$_2$

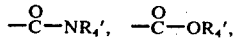

heterocyclic aliphatic, alkanoyloxyalkyl or —$NO_2$ wherein $R_4$ and $R_5$ are the same or different and are selected from alkyl or aryl.

The carbonyl compound may, for example, be an aldehyde or ketone e.g. formaldehyde, acetaldehyde, propionaldehyde, butyraldehyde, glycolaldehyde and glyoxylic esters, for example t-butyl glyoxylate.

The coupling reaction may be catalysed by a weak organic acid such as benzoic acid.

The reaction with the carbonyl compound may be carried out by vigorously stirring the components together e.g. at a temperature of from —30° to +100°C. When the reaction is effected at a temeprature at which one or more reactants may volatilise a closed system may be used. The reaction may be effected in an inert or relatively inert solvent, for example, a hologenated hydrocarbon, e.g. methylene chloride; a hydrocarbon e.g. benzene; an acyclic or cyclic ether e.g. diethyl ether, tetrahydrofuran or dioxan; dimethylsulphoxide; and amide e.g. dimethylformamide or dimethylacetamide or hexamethylphosphoramide.

It should be noted that when the 7β-acylamido group contains an amino group it will be necessary to protect this during the various reaction stages. The protecting group is conveniently one which can be removed by hydrolysis without affecting the rest of the molecule, especially the lactam and 7β-amido linkages. The amine protecting group and the esterifying group at the 4-COOH position can be removed using the same reagent. An advantageous procedure is to remove both groups at the last stage in the sequence. Protected amine groups include urethane, arylmethyl (e.g., trityl) amino, arylmethyleneamino, sulphenylamino or enamine types. Such groups can in general be removed by one or more reagents selected from dilute mineral acids, e.g. dilute hydrochloric acid, concentrated organic acids, e.g., concentrated acetic acid, trifluoroacetic acid, and liquid hydrogen bromide at very low temperature, e.g. —80°C. A convenient protecting group is the t-butoxycarbonyl group, which is readily removed by hydrolysis with dilute mineral acid, e.g. dilute hydrochloric acid, or preferably with a strong acid (e.g. formic acid, trifluoroacetic acid or liquid HF) e.g. at a temperature of 0–40°C. preferably at room temperature (15–25°C). Another convenient protecting group is the 2,2,2-trichloroethoxycarbonyl group which may be split off by an agent such as zinc/acetic acid, zinc/formic acid, zinc/lower alcohols or zinc/pyridine. The $NH_2$ group may also be protected as $NH_3^+$ by using the amino acid halide as its hydrohalide under conditions in which the amino group remains protonated.

Illustrative and representative of the preparation of an antibiotically useful 7-methoxy-3-vinyl cephalosporin utilizing the novel 7-methoxy 3-phosphoranylidene compounds of the invention is as follows Preparation of benzhydryl 3-(2-thienylvinyl)-7α-methoxy-7-β-(2-thienylacetamido)-3-cephem-4-carboxylate.

A solution of 309 mg. benzhydryl-7β-methoxy-7β-(2-thienylacetamido)-3-(triphenylphosphoranylidenemethyl)-ceph-3-em-4-carboxylate and 0.30 ml. thiophene-2-carboxaldehyde in 3ml. methylene chloride was stirred at 22° for 30 hrs. The reaction mixture was evaporated on a rotary evaporator and then on a vacuum pump to remove solvent and unreacted aldehyde. The residue was chromatographed on 7 g. Baker silica gel using benzene and benzene-ethyl acetate mixtures. The product, 122.6 mg., appeared with 10% ethyl acetate in benzene. The product was placed on 2-8 × 8 prep. t.l.c. plates, eluted with ethyl acetate/benzene : 1/3, and the main fraction was scraped from the plates and eluted with ethyl acetate to afford 105.5 mg. product. Yield = 43%.

Anal. Calcd. for $C_{33}H_{28}N_2O_5S_3$: C, 63.04; H, 4.49; N, 4.46. Found: C, 63.38; H, 4.36; N, 3.85. Mass spectrum: 628 (M+), 417, 208, 167.

Preparation of 3-(2-thienylvinyl)-7α-methoxy-7β-(2-thienylacetamido)-3-cephem-4-carboxylic acid.

To a solution of 84.2 mg. of benzhydryl 3-(2-thienylvinyl)-7α-methoxy-7β-(2-thienylacetamido)-3-cephem-4-carboxylate in 1 ml. anisole cooled in an ice bath was added 2 ml. ice cold trifluoroacetic acid. After 10 mins. at 0° the reaction solution was evaporated on a vacuum pump. The residue was slurried with 1 ml. anisole and reevaporated. The residue was washed twice with 4 ml. portions of boiling hexane/ether : 1/1. The insoluble residue of 66.7 mg. was dissolved in methylene chloride, filtered and reevaported. Yield 100 %. Nmr(CDCl₃): C₂H at 3.50; C₆H at 5.12 (s) and 5.19 (s); OC$\underline{H}_3$ at 3.53 (s).

Further representative of the 7-methoxy 3-vinyl cephalosporins that may be prepared via the reaction of a carbonyl compound and the novel 7-methoxy-3-phosphoranylidene starting materials in accordance with the above procedure are the following:

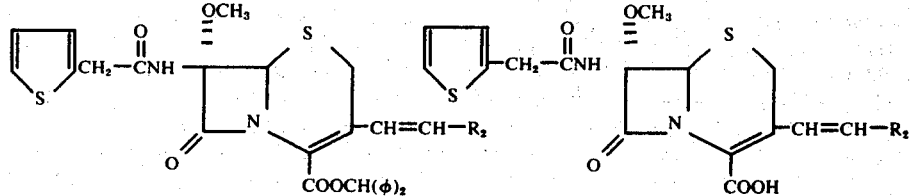

| Examples | Carbonyl Reagent R₂—CHO R₂ = | | |
|---|---|---|---|
| 12 | 4-thiazoyl | benzhydryl 3-(4-thiazoylvinyl)-7α-methoxy-7β-(2-thienylacetamido)-3-cephem-4-carboxylate<br><br>mass spectrum: 629 (m+), 614, 462, 418, 359, 248, 204, 167<br><br>Yield = 27% | 3-(4-thiazoylvinyl)-7α-methoxy-7β-(2-thienylacetamido)-3-cephem-4-carboxylic acid<br><br>nmr (CDCl₃)<br>C₂~3.40δ<br>C₆ 5.15δ (s)<br>—OCH₃ 3.48δ (s)<br>mass spectrum: 354, 293, 274, 253, 207<br>Yield = 76% |
| 13 | 4-pyridyl | benzhydryl 3-(4-pyridylvinyl)-7α-methoxy-7β-(2-thienylacetamido)-3-cephem-4-carboxylate<br><br>mass spectrum: 623 (m+), 608, 457, 412, 245, 201, 167<br>nmr (CDCl₃)<br>C₂ 3.05δ,~3.56<br>C₆ 5.08δ (s) and 5.13δ (s)<br>—OCH₃ 3.56δ<br>Yield = 48% | 3-(4-pyridylvinyl)-7α-methoxy-7β-(2-thienylacetamido)-3-cephem-4-carboxylic acid<br><br><br><br><br>Yield = 100% |
| 14 | 2-thienyl | benzhydryl 3-(2-thienylvinyl)-7α-methoxy-7β-(2-thienylacetamido)-3-cephem-4-carboxylate<br><br>mass spectrum: 628 (m+), 461, 417, 206, 167<br>nmr (CDCl₃)<br><br>C₂~3.45δ (AB)<br>C₆ 5.08δ (s) and 5.19 (s)<br>—OCH₃ 3.53 δ (s)<br>Yield = 43% | 3-(2-thienylvinyl)-7α-methoxy-7β-(2-thienylacetamido)-3-cephem-4-carboxylic acid<br><br>nmr (CDCl₃)<br><br>C₂~3.58δ<br>C₆ 5.12δ (s) and 5.19δ (s)<br><br>—OCH₃ 3.53δ (s)<br><br>Yield = 100% |
| 15 | acetoxymethyl | benzhydryl 3-[2-(acetoxymethyl)vinyl]-7α-methoxy-7β-(2-thienylacetamido)-3-cephem-4-carboxylate<br><br>CDCl₃ solution<br>C₂~3.36δ (multiplet pattern obscured by nearby peaks);<br>C₆ 5.22δ (s),<br>—CH₂O— 4.70–4.22δ (m), Ac— 2.00δ (s);<br>CH₃O— 3.52δ (s); C₃′ 6.55δ (d, 12 Hz); C₃″ 5.82–5.40δ (m).<br><br>Yield = 25% | 3-[2-(acetoxymethyl)vinyl]-7α-methoxy-7β-(2-thienylacetamido)-3-cephem-4-carboxylic acid<br><br>D₂O solution<br>C₂ 3.38δ (dd, 18 & 24 Hz);<br>C₆ 5.16δ (s),<br>—CH₂O—~4.6δ (obscured by HDP peak at 4.65δ);<br>Ac= 2.13δ (s); CH₃— 3.55δ (s);<br>C₃′ 6.18δ (d,J=10Hz); C₃″ 5.85–5.45 (m).<br>Yield = 87% |
| 16 | 2-methyl-1,3,4-thiadiazol-5-yl | benzhydryl 3-[2-(2-methyl-1,3,4-thiadiazol-5-yl)vinyl]-7α-methoxy-7β-(2-thienylacetamido)-3-cephem-4-carboxylate<br><br>C₂~3.5δ (obsecured by nearby peaks);<br>C₆ 5.20δ (s);<br>C—CH₃ 2.72δ (s); CH₃O— 3.55δ (s);<br>C₃′ & C₃″ amongst φ₂CH— and thienyl multiplets<br>Yield = 15% | 3-[2-(2-methyl-1,3,4-thiadiazol-5-yl)-vinyl]-7α-methoxy-7β-(2-thienyl-acetamido)-3-cephem-4-carboxylic acid<br><br>C₂ & CH₃O— 3.55 (b);<br>C₆ 5.22δ (s);<br>C—CH₃ 2.08δ; C₃′, C₃″, and thienyl 7.44–6.57 (m)<br><br>Yield = 15%<br>(Sample contaminated with aldehyde; gave overall of 15%, so must have had at least as good conversion in first step.) |
| 17 | 1-oxo-4-pyridyl | benzhydryl 3-(1-oxo-4-pyridylvinyl)-7α-methoxy-7β-(2-thienylacetamido)-3-cephem-4-carboxylate<br><br>nmrδ 3.45 (,C₂), 3.50 (s, CH₃O), 3.90 (s, thiophene CH₂) 5.10 (s,C₆) 7.03 (m, thiophene), 7.35 (s, benzhydryl) 8.07 (t, pyridyl). vinyls).<br>NMR (CDCl₃)<br>Yield =52% | 3-(1-oxo-4-pyridylvinyl)-7α-methoxy-7β-(2-thienylacetamido)-3-cephem-4-carboxylic acid<br><br>nmr δ 3.40 (S, OMe), 3.75 (s,C₂), 3.85 (s, thiophene CH₂), 5.25 (s,C₆), 7.0–8.25 (pyridyl thiophenes and<br><br>NMR (DMSO-d₆)<br>Yield = 75% |

The 3-vinyl cephalosporins that are prepared via the novel starting materials of the invention are valuable antibiotics active against various gram-positive and gram-negative bacteria and, accordingly, find utility in human and veterinary medicine. The vinyl compounds can therefore be used as antibacterial drugs for treating infections caused by gram-positive or gram-negative bacteria, for example against *Staphylococcus aureus* (penicillin resistant), *Escherichia coli*, *Klebsiella pneumoniae*, *Salmonella typhosa*, *Pseudomonas* and *Bacterium proteus*. The antibacterial cephalosporins may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The 3-vinyl cephalosporins invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose aluminum stearate gel or hydrogenated edible fats; emulsifying agents, for example lecithin, sorbitan monooleate or acacia; non-aqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride. Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder of liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

Compositions containing the 3-vinyl cephalosporins may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

What is claimed is:

1. Compounds of the formula:

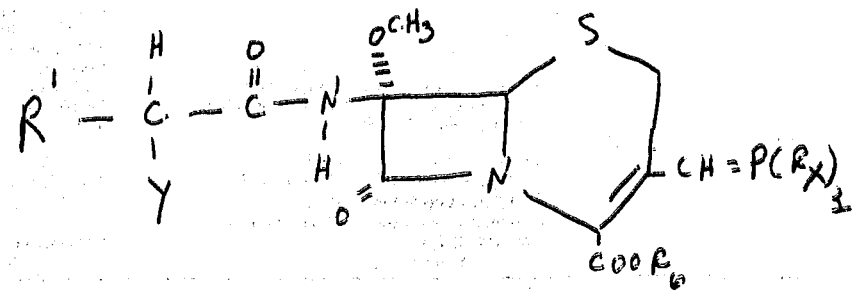

wherein R' is phenyl or thienyl; and y is Hydrogen, amino or carboxy.

2. The compound of claim 1 wherein R' is thienyl and Y is hydrogen.

3. The compound of claim 1 wherein R' is phenyl and Y is $NH_2$.

4. The compound of claim 1 wherein R' is thienyl and Y is $CO_2H$.

\* \* \* \* \*